(12) United States Patent
Luo et al.

(10) Patent No.: US 8,067,656 B2
(45) Date of Patent: Nov. 29, 2011

(54) LIQUID-LIQUID SEPARATION PROCESS VIA COALESCERS

(75) Inventors: Huping Luo, Richmond, CA (US);
Moinuddin Ahmed, Hercules, CA (US);
Krishniah Parimi, Alamo, CA (US);
Bong-Kyu Chang, Novato, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 434 days.

(21) Appl. No.: 12/324,601

(22) Filed: Nov. 26, 2008

(65) Prior Publication Data
US 2010/0130800 A1 May 27, 2010

(51) Int. Cl.
*C07C 2/58* (2006.01)
*C07C 2/60* (2006.01)
*C07C 7/12* (2006.01)
*B01J 38/56* (2006.01)

(52) U.S. Cl. ........ 585/709; 585/718; 585/721; 585/818; 502/31

(58) Field of Classification Search ............ 502/31; 585/709, 718, 721, 818
See application file for complete search history.

(56) References Cited

U.S. PATENT DOCUMENTS

| | | | |
|---|---|---|---|
| 5,500,132 A | 3/1996 | Elmi | |
| 5,681,462 A | 10/1997 | Brockhoff et al. | |
| 5,750,455 A | 5/1998 | Chauvin et al. | |
| 6,028,024 A | 2/2000 | Hirschauer et al. | |
| 2001/0047967 A1 | 12/2001 | Williamson et al. | |
| 2003/0060359 A1 | 3/2003 | Olivier-Bourbigou et al. | |
| 2004/0077914 A1 | 4/2004 | Zavilla et al. | |
| 2006/0131209 A1 | 6/2006 | Timken et al. | |
| 2006/0135839 A1 | 6/2006 | Elomari et al. | |
| 2007/0142213 A1* | 6/2007 | Elomari et al. ........ | 502/53 |

FOREIGN PATENT DOCUMENTS

WO    WO 2008/056111    * 5/2008

OTHER PUBLICATIONS

PCT/US2009/0665820. PCT International Preliminary Report on Patentability, mailed Jun. 9, 2011.
PCT/US2009/055820, PCT Search Report and Written Opinion filing date Nov. 24, 2009, 7 pages.

* cited by examiner

*Primary Examiner* — Elizabeth Wood
(74) *Attorney, Agent, or Firm* — Merchant & Gould

(57) ABSTRACT

A process for separating an ionic liquid from hydrocarbons employs a coalescer material having a stronger affinity for the ionic liquid than the hydrocarbons. The coalescer material can be a high surface area material having a large amount of contact area to which ionic liquid droplets dispersed in the hydrocarbons may adhere. The process includes feeding a mixture comprising ionic liquid droplets dispersed in hydrocarbons to a coalescer comprising the coalescer material. The process further includes a capture step involving adhering at least a portion of the ionic liquid droplets to the coalescer material to provide captured droplets and a coalescing step involving coalescing captured droplets into coalesced droplets. After the capture and coalescence steps, the coalesced droplets are allowed to fall from the coalescer material to separate the ionic liquid from the hydrocarbons and provide a hydrocarbon effluent.

24 Claims, 4 Drawing Sheets

US 8,067,656 B2

LIQUID-LIQUID SEPARATION PROCESS VIA COALESCERS

FIELD OF ART

The present disclosure relates to a process for separating an ionic liquid from hydrocarbons by the use of a coalescer. More particularly, the present disclosure relates to removing an ionic liquid catalyst from hydrocarbons (e.g. a product produced during an alkylation reaction catalyzed by the ionic liquid catalyst) by the use of a coalescer.

BACKGROUND

An alkylation process, which is disclosed in U.S. Patent Application Publication 2006/0131209 ("the '209 publication"), involves contacting isoparaffins, preferably isopentane, with olefins, preferably ethylene, in the presence of an ionic liquid catalyst to produce gasoline blending components. The contents of the '209 publication are incorporated by reference herein in its entirety.

An ionic liquid catalyst distinguishes this novel alkylation process from conventional processes that convert light paraffins and light olefins to more lucrative products such as the alkylation of isoparaffins with olefins and the polymerization of olefins. For example, two of the more extensively used processes to alkylate isobutane with $C_3$-$C_5$ olefins to make gasoline cuts with high octane numbers use sulfuric acid ($H_2SO_4$) and hydrofluoric acid (HF) catalysts.

Ionic liquid catalysts specifically useful in the alkylation process described in the '209 publication are disclosed in U.S. Patent Application Publication 2006/0135839 ("the '839 publication"), which is also incorporated by reference in its entirety herein. Such catalysts include a chloroaluminate ionic liquid catalyst comprising a hydrocarbyl substituted pyridinium halide and aluminum trichloride or a hydrocarbyl substituted imidazolium halide and aluminum trichloride. Such catalysts further include chloroaluminate ionic liquid catalysts comprising an alkyl substituted pyridinium halide and aluminum trichloride or an alkyl substituted imidazolium halide and aluminum trichloride. Preferred chloroaluminate ionic liquid catalysts include 1-butyl-4-methyl-pyridinium chloroaluminate (BMP), 1-butyl-pyridinium chloroaluminate (BP), 1-butyl-3-methyl-imidazolium chloroaluminate (BMIM) and 1-H-pyridinium chloroaluminate (HP).

However, ionic liquid catalysts have unique properties making it necessary to further develop and modify the ionic liquid catalyzed alkylation process in order to achieve superior gasoline blending component products, improved process operability and reliability, reduced operating costs, etc.

There is a need for an effective and efficient process for removing ionic liquid from the hydrocarbon phase after ionic liquid catalyzed alkylation. In general, the process should be simple and efficient enough to be used to separate any ionic liquid, not just an ionic liquid catalyst, from hydrocarbons where the density of the hydrocarbons is less than the density of the ionic liquid.

SUMMARY

Disclosed herein is a process for separating an ionic liquid from hydrocarbons using a coalescer.

In one embodiment, a process for separating an ionic liquid from hydrocarbons comprises: (a) feeding a mixture comprising hydrocarbons and ionic liquid to a coalescer, the hydrocarbons having ionic liquid droplets dispersed therein, and the coalescer comprising a coalescer material; (b) adhering at least a portion of the ionic liquid droplets to the coalescer material to provide captured droplets; (c) coalescing captured droplets into coalesced droplets; and (d) allowing the coalesced droplets to fall from the coalescer material to separate the ionic liquid from the hydrocarbons and provide a hydrocarbon effluent, wherein the coalescer material has a stronger affinity for the ionic liquid than the hydrocarbons.

In another embodiment, a process for separating an ionic liquid from hydrocarbons comprises: (a) feeding a mixture comprising hydrocarbons and ionic liquid to a coalescer, the hydrocarbons having ionic liquid droplets dispersed therein, and the coalescer comprising a coalescer material; (b) adhering at least a portion of the ionic liquid droplets to the coalescer material to provide captured droplets; (c) coalescing the captured droplets into coalesced droplets; (d) settling the coalesced droplets to provide an ionic liquid layer; (e) removing the ionic liquid layer from the coalescer; and (f) removing the hydrocarbons from the coalescer to provide a hydrocarbon effluent, wherein the coalescer material has a stronger attraction for the ionic liquid than the hydrocarbons.

The separation process as disclosed herein can be utilized in a process for regenerating an ionic liquid catalyst and an alkylation process. Accordingly, also disclosed herein is a process for regenerating an ionic liquid catalyst and an alkylation process.

A process for regenerating an ionic liquid catalyst comprises: (a) feeding a mixture comprising a spent ionic liquid catalyst and hydrocarbons to a coalescer, the hydrocarbons having spent ionic liquid catalyst droplets dispersed therein, and the coalescer comprising a coalescer material; (b) adhering at least a portion of the spent ionic liquid catalyst droplets to the coalescer material to provide captured droplets; (c) coalescing the captured droplets into coalesced droplets; (d) settling the coalesced droplets to provide a spent ionic liquid catalyst layer; (e) removing the spent ionic liquid catalyst layer from the coalescer to provide a spent ionic liquid catalyst stream; (f) removing the hydrocarbons from the coalescer to provide a hydrocarbon effluent; and (g) regenerating the spent ionic liquid catalyst stream to provide regenerated ionic liquid catalyst; wherein the coalescer material has a stronger attraction for the spent ionic liquid catalyst than the hydrocarbons.

An alkylation process comprises: (a) conducting an alkylation reaction in the presence of an ionic liquid catalyst to provide an alkylation product and a spent ionic liquid catalyst; (b) feeding a mixture comprising the spent ionic liquid catalyst and the alkylation product to a coalescer, the alkylation product having spent ionic liquid catalyst droplets dispersed therein, and the coalescer comprising a coalescer material; (c) coalescing the captured droplets into coalesced droplets; (d) settling the coalesced droplets to provide a spent ionic liquid catalyst layer; (e) removing the spent ionic liquid catalyst layer from the coalescer to provide a spent ionic liquid catalyst stream; (f) removing the alkylation product from the coalescer to provide an alkylation effluent; (g) regenerating the spent ionic liquid catalyst stream to provide regenerated ionic liquid catalyst; and (h) recycling the regenerated ionic liquid catalyst to the alkylation reaction step (a), wherein the coalescer material has a stronger attraction for the spent ionic liquid catalyst than the alkylation product.

Among other factors, the separation process as disclosed herein permits separation of a near stable emulsion of ionic liquid droplets in a bulk phase of hydrocarbons. As used herein, the term "near stable emulsion" refers to an emulsion in which the droplets dispersed in the bulk phase are sufficiently small that it takes between about 8 and about 12 hours for the emulsion to separate by gravity. The separation process also permits separation of ionic liquid droplets that separate more quickly from an ionic liquid/hydrocarbon emulsion. Both the ionic liquid droplets that form a near stable emulsion and the ionic liquid droplets that separate more quickly may be separated from the hydrocarbon bulk phase in a reasonable amount of time. For both the ionic liquid droplets that form a near stable emulsion and the ionic liquid droplets that separate more quickly, this amount of time is less than the amount of time required for any separation of the ionic liquid/hydrocarbons that is possible by gravity decantation.

DETAILED DESCRIPTION

Figure 1:
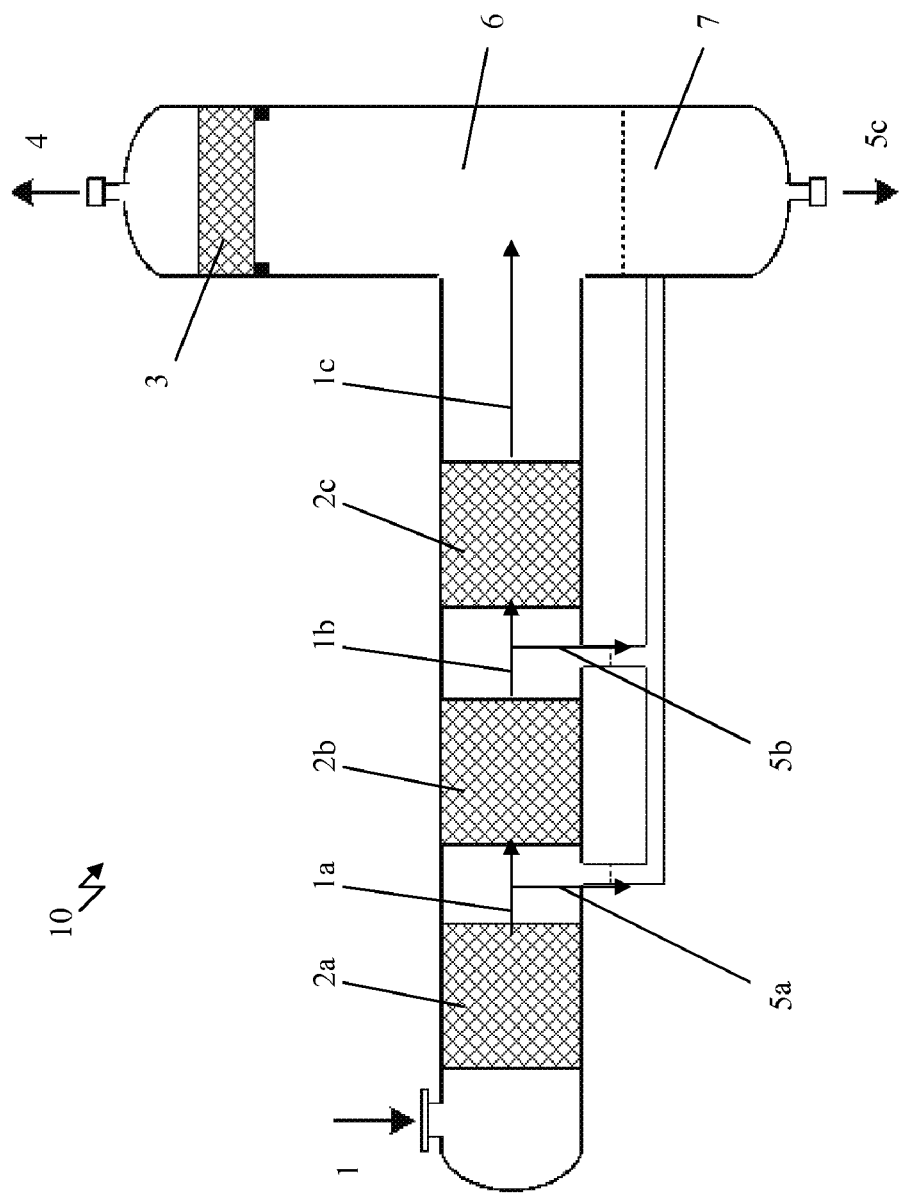
FIG. 1 is a schematic illustration of a process as disclosed herein for separating an ionic liquid from hydrocarbons by the use of a coalescer having multiple stages configured in series.

Process for Separating an Ionic Liquid from Hydrocarbons

In its broadest aspect, the present process involves separating an ionic liquid from hydrocarbons in a coalescer. A coalescer is known in the art as a vessel that facilitates separation of two liquids. It enhances gravitational settling of a liquid by the use of coalescing media. As such, liquid separation in a coalescer is much faster than liquid separation in a gravity decanter. It has been discovered that a coalescer can be successfully used in separating ionic liquid droplets suspended in a hydrocarbon phase.

The coalescer used in the present process contains a coalescer material, which has a stronger affinity for the ionic liquid than the hydrocarbons. Therefore, the ionic liquid preferentially adheres to the coalescer material.

According to the present process, a mixture comprising hydrocarbons and ionic liquid is fed to a coalescer. The ionic liquid is in the form of droplets dispersed in a hydrocarbon bulk phase. Inside the coalescer, the ionic liquid droplets are drawn to and adhere to the coalescer material. The droplets adhered to the coalescer material are referred to herein as "captured droplets." As more and more captured droplets accumulate on the coalescer material, they coalesce (i.e. unite or combine into), by attractive forces, into larger droplets in order to minimize their interfacial energy. These larger droplets of ionic liquid, still adhered to the coalescer material, are referred to herein as "coalesced droplets." Due to their larger size, the coalesced droplets eventually detach and fall away from the coalescer material. Such detachment and falling away permits the ionic liquid to separate from the hydrocarbons thereby providing a hydrocarbon effluent.

Accordingly, in its broadest aspect, the present process comprises: (a) feeding a mixture comprising hydrocarbons and ionic liquid to a coalescer, the hydrocarbons having ionic liquid droplets dispersed therein, and the coalescer comprising a coalescer material; (b) adhering at least a portion of the ionic liquid droplets to the coalescer material to provide captured droplets; (c) coalescing captured droplets into coalesced droplets; and (d) allowing the coalesced droplets to fall from the coalescer material to separate the ionic liquid from the hydrocarbons and provide a hydrocarbon effluent, wherein the coalescer material has a stronger affinity for the ionic liquid than the hydrocarbons.

Generally, the coalesced droplets fall through the hydrocarbon bulk phase by gravitational forces and settle to a bottom portion of the coalescer forming a layer of ionic liquid at the bottom of the coalescer. The hydrocarbon bulk phase remains on top of this layer of ionic liquid. Thus, according to a further aspect of the present process, the fallen coalesced droplets provide an ionic liquid layer. This ionic liquid layer can then be removed from the coalescer. Similarly, the hydrocarbons can be removed from the coalescer to provide a hydrocarbon effluent.

Accordingly, in another aspect, the process for separating an ionic liquid from hydrocarbon comprises: (a) feeding a mixture comprising hydrocarbons and ionic liquid to a coalescer, the hydrocarbons having ionic liquid droplets dispersed therein, and the coalescer comprising a coalescer material; (b) adhering at least a portion of the ionic liquid droplets to the coalescer material to provide captured droplets; (c) coalescing the captured droplets into coalesced droplets; (d) settling the coalesced droplets to provide an ionic liquid layer; (e) removing the ionic liquid layer from the coalescer; and (f) removing the hydrocarbons from the coalescer to provide a hydrocarbon effluent, wherein the coalescer material has a stronger attraction for the ionic liquid than the hydrocarbons.

The process as disclosed herein is useful to recover an ionic liquid catalyst for recycling to any process in which the ionic liquid catalyst is used as a catalyst. After the ionic liquid is separated from the hydrocarbons, it can be returned to any reaction process, for example, an alkylation process.

One of the unique properties of an ionic liquid catalyst is its much higher activity in catalyzing alkylation reactions than conventional sulfuric acid and hydrofluoric acid catalysts.

In conventional alkylation processes, due to relatively low catalyst activity, a large amount of acid catalyst has to be used in the system, for example, 50-60 vol %. As a result, the acid catalyst forms a continuous phase in the alkylation reactor while the hydrocarbon reactants (i.e., isoparaffin and olefin) form a dispersed phase or small droplets suspended in the acid phase. In this liquid-liquid dispersion, a large interfacial area between the catalyst continuous phase and the hydrocarbon dispersed phase can be achieved by conventional emulsifying techniques, such as high speed stirring and static mixing.

In contrast, in the ionic liquid alkylation process, a much smaller amount of ionic liquid catalyst is needed to catalyze the reactions with high selectivity. Usually, a 5-10 vol % of ionic liquid catalyst is sufficient to catalyze the reactions between isoparaffin and olefin. Under such conditions, the hydrocarbon phase forms a continuous phase while the ionic liquid forms a dispersed phase or small droplets suspended in the hydrocarbon phase. This liquid-liquid dispersion requires highly intimate contact between the catalyst and the hydrocarbon phases. In short, the ionic liquid and hydrocarbon phase must be emulsified to achieve intimate contact between the ionic liquid and hydrocarbon phase for greater alkylation product quality and reaction control.

After alkylation, the ionic liquid and the hydrocarbon phase, the majority of which is alkylation product, must be separated. Due to the large density difference between the ionic liquid and hydrocarbon phase, the ionic liquid may generally be separated from the hydrocarbon phase by gravity decantation. However, gravity separation is only efficient and effective if the ionic liquid droplets in the emulsion are sufficiently large such that they will settle out of the hydrocarbon phase and will settle out of the hydrocarbon phase in a reasonable amount of time. It has been discovered, since the ionic liquid catalyzed alkylation process requires intimate contact between the ionic liquid and hydrocarbon phase, some of the ionic liquid droplets may be so small that they form a near stable emulsion.

Accordingly, it has been further discovered that the present process is particularly useful for separating such near stable emulsions of ionic liquid catalyst in a bulk hydrocarbon phase.

The process as disclosed herein is also useful to regenerate an ionic liquid catalyst that has been at least partially deactivated. Such a catalyst is referred to herein as a "spent ionic liquid catalyst." The spent ionic liquid catalyst can be either partially deactivated or fully deactivated.

An ionic liquid catalyst can be used to generate hydrocarbons, for example, an alkylation product. In order to subject a spent ionic liquid catalyst to a regeneration process, the spent ionic liquid catalyst must be efficiently and effectively separated from the hydrocarbons, produced by the spent ionic liquid catalyst. Accordingly, as with any ionic liquid, a mixture having a spent ionic liquid catalyst droplets dispersed in a hydrocarbon bulk phase can be fed to a coalescer comprising a coalescer material. In the coalescer, a capture step occurs in which at least a portion of the spent ionic liquid catalyst droplets adhere to the coalescer material to provide captured droplets. As discussed above, the coalescer material has a stronger attraction for the spent ionic liquid catalyst than the hydrocarbons such that the spent ionic liquid catalyst droplets adhere more readily to the coalescer material than the hydrocarbons. Next, in the coalescer, a coalescence step occurs whereby captured droplets coalesce (i.e. unite or combine into), by attractive forces, into larger coalesced droplets of spent ionic liquid catalyst in order to minimize their interfacial energy. These larger, coalesced droplets then detach and fall away from the coalescer material. They proceed to settle by gravitational forces through the hydrocarbon phase to provide a layer of spent ionic liquid catalyst in the coalescer. The bulk hydrocarbon phase remains in a layer on top of the spent ionic liquid catalyst layer. This spent ionic liquid catalyst layer can then be removed from the coalescer to provide a spent ionic liquid catalyst stream and the hydrocarbons can be removed from the coalescer to provide a hydrocarbon effluent. After such separation, the spent ionic liquid catalyst stream can be regenerated to provide regenerated ionic liquid catalyst.

Additionally, the process as disclosed herein can also be incorporated into an alkylation process. An alkylation process may require an ionic liquid catalyst to produce an alkylation product. The ionic liquid catalyst, however, may remain dispersed as droplets in a bulk phase of the alkylation product and need to be separated from such alkylation product. The ionic liquid catalyst dispersed within the alkylation product may be at least partially deactivated such that it is a spent ionic liquid catalyst.

If the process is incorporated into an alkylation process, an alkylation reaction can be conducted in the presence of an ionic liquid catalyst to provide an alkylation product and a spent ionic liquid catalyst. As with any ionic liquid, a mixture having spent ionic liquid catalyst droplets dispersed in a bulk phase of alkylation product can be fed to a coalescer comprising a coalescer material. In the coalescer, a capture step occurs in which at least a portion of the spent ionic liquid catalyst droplets adhere to the coalescer material to provide captured droplets. As discussed above, the coalescer material has a stronger attraction for the spent ionic liquid catalyst than the alkylation product such that the spent ionic liquid catalyst droplets adhere more readily to the coalescer material than the alkylation product. Next, in the coalescer, a coalescence step occurs whereby captured droplets coalesce (i.e. unite or combine into), by attractive forces, into larger coalesced droplets of spent ionic liquid catalyst in order to minimize their interfacial energy. These larger, coalesced droplets then detach and fall away from the coalescer material. They proceed to settle by gravitational forces through the alkylation product to provide a layer of spent ionic liquid catalyst in the coalescer. The alkylation product remains in a layer on top of the spent ionic liquid catalyst layer. This spent ionic liquid catalyst layer can then be removed from the coalescer to provide a spent ionic liquid catalyst stream and the alkylation product can be removed from the coalescer to provide an alkylation effluent. After such separation, the spent ionic liquid catalyst stream can be regenerated to provide regenerated ionic liquid catalyst, which is subsequently recycled to the alkylation reaction.

Ionic Liquid Droplets

As used herein, the term "ionic liquids" refers to liquids that are composed entirely of ions as a combination of cations and anions. The term "ionic liquids" includes low-temperature ionic liquids, which are generally organic salts with melting points under 100° C. and often even lower than room temperature.

Ionic liquids may be suitable, for example, for use as a catalyst and as a solvent in alkylation and polymerization reactions as well as in dimerization, oligomerization, acetylation, olefin metathesis, and copolymerization reactions. The present embodiments are useful with regard to any ionic liquid catalyst.

One class of ionic liquids is fused salt compositions, which are molten at low temperature and are useful as catalysts, solvents, and electrolytes. Such compositions are mixtures of components, which are liquid at temperatures below the individual melting points of the components.

The most common ionic liquids are those prepared from organic-based cations and inorganic or organic anions. The most common organic cations are ammonium cations, but phosphonium and sulphonium cations are also frequently used. Ionic liquids of pyridinium and imidazolium are perhaps the most commonly used cations. Anions include, but are not limited to, $BF_4^-$, $PF_6^-$, haloaluminates such as $Al_2Cl_7^-$ and $Al_2Br_7^-$, $[(CF_3SO_2)_2N]^-$, alkyl sulphates ($RSO_3^-$), carboxylates ($RCO_2^-$) and many others. The most catalytically interesting ionic liquids for acid catalysis are those derived from ammonium halides and Lewis acids (such as $AlCl_3$, $TiCl_4$, $SnCl_4$, $FeCl_3$, etc.). Chloroaluminate ionic liquids are perhaps the most commonly used ionic liquid catalyst systems for acid-catalyzed reactions.

Examples of such low temperature ionic liquids or molten fused salts are the chloroaluminate salts. Alkyl imidazolium or pyridinium chlorides, for example, can be mixed with aluminum trichloride ($AlCl_3$) to form the fused chloroaluminate salts.

The ionic liquid droplets present in the hydrocarbon bulk phase can vary in size. In one embodiment of the present process, the ionic liquid droplets can have diameters between about 1 and about 1000 microns. In another embodiment, the ionic liquid droplets can have diameters between about 4 microns and about 200 microns. In further embodiment, the ionic liquid droplets can have diameters of about 50 microns or greater. In yet another embodiment, the ionic liquid droplets can have diameters of about 5 microns or greater.

Droplet size is dependent upon the manner in which the ionic liquid becomes dispersed within the hydrocarbons. For example, if the ionic liquid is an ionic liquid catalyst, for some reactions, the ionic liquid can be contacted with reactants in a continuously-stirred tank reactor (CSTR) to provide a hydrocarbon product. For other reactions, the ionic liquid can be dispersed through nozzles to contact reactants. Nozzle dispersion generally provides ionic liquid droplets smaller than those present in a CSTR. In fact, ionic liquid droplets in a CSTR may have diameters of about 50 microns or greater, while ionic liquid droplets generated by nozzles may have diameters of about 5 microns or greater.

The ionic liquid droplets may be spherical. However, the ionic liquid droplets, especially larger ionic liquid droplets, may not be spherical. Accordingly, the term "diameter" as used herein refers to the diameter of spherical droplets and the longest dimension of non-spherical droplets.

In general, the ionic liquid droplets may comprise between 0% and about 10% by volume of the mixture, comprising hydrocarbons and ionic liquid, which enters the coalescer.

In one embodiment, the ionic liquid droplets may also comprise between about 1% and about 10% by volume of the mixture, comprising hydrocarbons and ionic liquid, which enters the coalescer.

In one embodiment, the ionic liquid is an ionic liquid catalyst. The process as described herein can employ a catalyst composition comprising at least one aluminum halide such as aluminum chloride, at least one quaternary ammonium halide and/or at least one amine halohydrate, and at least one cuprous compound. Such a catalyst composition and its preparation is disclosed in U.S. Pat. No. 5,750,455, which is incorporated by reference in its entirety herein.

Alternatively, the ionic liquid catalyst can be a chloroaluminate ionic liquid catalyst. For example, the ionic liquid catalyst can be a pyridinium or imidazolium-based chloroaluminate ionic liquid. These ionic liquids have been found to be much more effective in the alkylation of isopentane with ethylene than aliphatic ammonium chloroaluminate ionic liquid (such as tributyl-methyl-ammonium chloroaluminate). The ionic liquid catalyst can be (1) a chloroaluminate ionic liquid catalyst comprising a hydrocarbyl substituted pyridinium halide of the general formula A below and aluminum trichloride or (2) a chloroaluminate ionic liquid catalyst comprising a hydrocarbyl substituted imidazolium halide of the general formula B below and aluminum trichloride. Such a chloroaluminate ionic liquid catalyst can be prepared by combining 1 molar equivalent hydrocarbyl substituted pyridinium halide or hydrocarbyl substituted imidazolium halide with 2 molar equivalents aluminum trichloride. The ionic liquid catalyst can also be (1) a chloroaluminate ionic liquid catalyst comprising an alkyl substituted pyridinium halide of the general formula A below and aluminum trichloride or (2) a chloroaluminate ionic liquid catalyst comprising an alkyl substituted imidazolium halide of the general formula B below and aluminum trichloride. Such a chloroaluminate ionic liquid catalyst can be prepared by combining 1 molar equivalent alkyl substituted pyridinium halide or alkyl substituted imidazolium halide to 2 molar equivalents of aluminum trichloride.

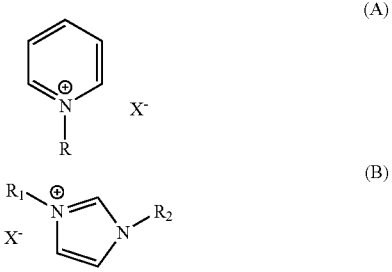

wherein R=H, methyl, ethyl, propyl, butyl, pentyl or hexyl group and X is a halo aluminate, and $R_1$ and $R_2$=H, methyl, ethyl, propyl, butyl, pentyl, or hexyl group and where $R_1$ and $R_2$ may or may not be the same. In one embodiment, the haloaluminate is a chloroaluminate.

The ionic liquid catalyst can also be mixtures of these chloroaluminate ionic liquid catalysts. Examples of chloroaluminate ionic liquid catalysts are 1-butyl-4-methyl-pyridinium chloroaluminate (BMP), 1-butyl-pyridinium chloroaluminate (BP), 1-butyl-3-methyl-imidazolium chloroaluminate (BMIM), 1-H-pyridinium chloroaluminate (HP), and N-butylpyridinium chloroaluminate ($C_5H_5NC_4H_9Al_2Cl_7$), and mixtures thereof.

A metal halide may be employed as a co-catalyst to modify the catalyst activity and selectivity. Commonly used halides for such purposes include NaCl, LiCl, KCl, $BeCl_2$, $CaCl_2$, $BaCl_2$, $SiCl_2$, $MgCl_2$, $PbCl_2$, CuCl, $ZrCl_4$, and AgCl as published by Roebuck and Evering (Ind. Eng. Chem. Prod. Res. Develop., Vol. 9, 77, 1970), which is incorporated by reference in its entirety herein. Especially useful metal halides are CuCl, AgCl, $PbCl_2$, LiCl, and $ZrCl_4$. Another useful metal halide is $AlCl_3$.

HCl or any Broensted acid may be employed as an effective co-catalyst to enhance the activity of the catalyst by boosting the overall acidity of the ionic liquid-based catalyst. The use of such co-catalysts and ionic liquid catalysts that are useful in practicing the present process are disclosed in U.S. Published Patent Application Nos. 2003/0060359 and 2004/0077914, the disclosures of which are herein incorporated by reference in their entirety. Other co-catalysts that may be used to enhance the catalytic activity of the ionic liquid catalyst include IVB metal compounds. In one embodiment, the co-catalysts include IVB metal halides such as $TiCl_3$, $TiCl_4$, $TiBr_3$, $TiBr_4$, $ZrCl_4$, $ZrBr_4$, $HfC_4$, and $HfBr_4$ as described by Hirschauer et al. in U.S. Pat. No. 6,028,024, which document is incorporated by reference in its entirety herein.

Hydrocarbons

The hydrocarbons sent to the coalescer can be a product, a reactant, or a mixture thereof. For example, the hydrocarbons can be an alkylation product.

Hydrocarbon Effluent

In one embodiment of the present process, the hydrocarbon effluent (i.e. hydrocarbons after separation from the ionic liquid) comprises 20 ppm or less of the ionic liquid. In another embodiment, the hydrocarbon effluent comprises 40 ppm or less of the ionic liquid. In yet another embodiment, the hydrocarbon effluent comprises 10 ppm or less of the ionic liquid.

Coalescer Material

The coalescer material has a stronger attraction for the ionic liquid than the hydrocarbons. The surface properties of the coalescer material should be such that the coalescer material can be fully wetted by the ionic liquid.

It is advantageous for the coalescer material to have a high specific surface area and, therefore, the coalescer material should have voids or openings of a size approaching the smallest droplet that must be removed. High specific surface area provides more area for the ionic liquid droplets to contact and increases the probability that the ionic liquid droplets will adhere to the coalescer material. Accordingly, high specific surface area also provides an increased number of captured droplets for coalescence into coalesced droplets.

Coalescer materials useful in the process disclosed herein include glass beads, stainless steel metal packing, fiberglass, polymer fibers, ceramic membrane, and mixtures thereof. For example, the coalescer material can be fiberglass. Fiberglass and polymer fibers have been found to be particularly effective coalescer materials due to their high specific surface area.

Residence Time

The residence time of the ionic liquid/hydrocarbon mixture in the process described herein can be less than about 2 hours. However, the residence time of the ionic liquid/hydrocarbon mixture in the process described herein can also be between about 1 minute and about 20 minutes. In one embodiment, the residence time of the ionic liquid/hydrocarbon mixture in the process described herein can be between about 1 minute and about 7 minutes.

The residence time is dependent upon the amount and size of the ionic liquid droplets and the specific surface area of the coalescer material. High specific surface area materials such as fiberglass and polymer fibers will require less residence time.

Multiple Stages

Multiple stages of coalescer material may be used to separate the ionic liquid from the hydrocarbons. The multiple stages can be oriented in series, in parallel, or both.

When oriented in series, each of the multiple stages can include different types of coalescer materials or the same type of coalescer material. Whether the type of coalescer material varies among the various stages or remains the same, the coalescer materials of each of the multiple stages can have voids or openings of different sizes. In earlier stages, the coalescer material can have voids or openings of a size suited to capturing larger droplets. In later stages, the coalescer material can have voids or openings of a size suited to capturing smaller droplets. Also, a portion of the ionic liquid captured and coalesced in a particular stage can be removed prior to sending the ionic liquid/hydrocarbon mixture to the next stage.

FIG. 1 illustrates an embodiment of the process as described herein having multiple stages oriented in series. As depicted in FIG. 1, a mixture 1 having ionic liquid droplets dispersed in a bulk phase of hydrocarbons is fed to a coalescer 10. The coalescer includes several stages 2a, 2b, 2c of coalescer material. The mixture first meets stage 2a. In stage 2a, capture and coalescence of at least a portion of the ionic liquid droplets occurs to provide captured droplets and coalesced droplets. An ionic liquid/hydrocarbon mixture 1a exits stage 2a and enters stage 2b, while a portion of the coalesced ionic liquid droplets fall out of the ionic liquid/hydrocarbon mixture as stream 5a. In stage 2b, capture and coalescence of at least a portion of ionic liquid droplets that have not been captured and coalesced occurs to provide additional captured droplets and coalesced droplets. An ionic liquid/hydrocarbon mixture 1b exits stage 2b and enters stage 2c, while a portion of the coalesced ionic liquid droplets fall out of the ionic liquid/hydrocarbon mixture as stream 5b. In stage 2c, capture and coalescence of at least a portion of ionic liquid droplets that have not been captured and coalesced occurs to provide even more captured and coalesced droplets.

Coalesced droplets that fall from the coalescer material of stages 2a, 2b and do not fall out of the ionic liquid/hydrocarbon mixture as streams 5a and 5b, as well as coalesced droplets that fall from the coalescer material of stage 2c, emerge from the final stage in a stream 1c of hydrocarbons and ionic liquid. This stream 1c enters a settling zone 6 of the coalescer. In the settling zone 6, the coalesced droplets drop through the hydrocarbons due to gravitational forces and settle into an ionic liquid layer 7 at the bottom of the settling zone. Ionic liquid from streams 5a and 5b combines with the ionic liquid layer 7, which exits the coalescer 10 to provide an ionic liquid stream 5c. Hydrocarbons exit the settling zone 6 to provide a hydrocarbon effluent 4.

As shown in FIG. 1, the coalescer 10 can further include an additional stage 3 of coalescer material in the settling zone 6. This stage 3 is useful to prevent any ionic liquid droplets that have not been captured and coalesced in stages 2a, 2b, 2c from exiting the coalescer 10 in the hydrocarbon effluent 4. It acts to capture and coalesce ionic liquid droplets in the same manner as stages 2a, 2b, 2c.

When oriented in parallel, the multiple stages can increase the overall capacity of the process as disclosed herein.

Figure 2:
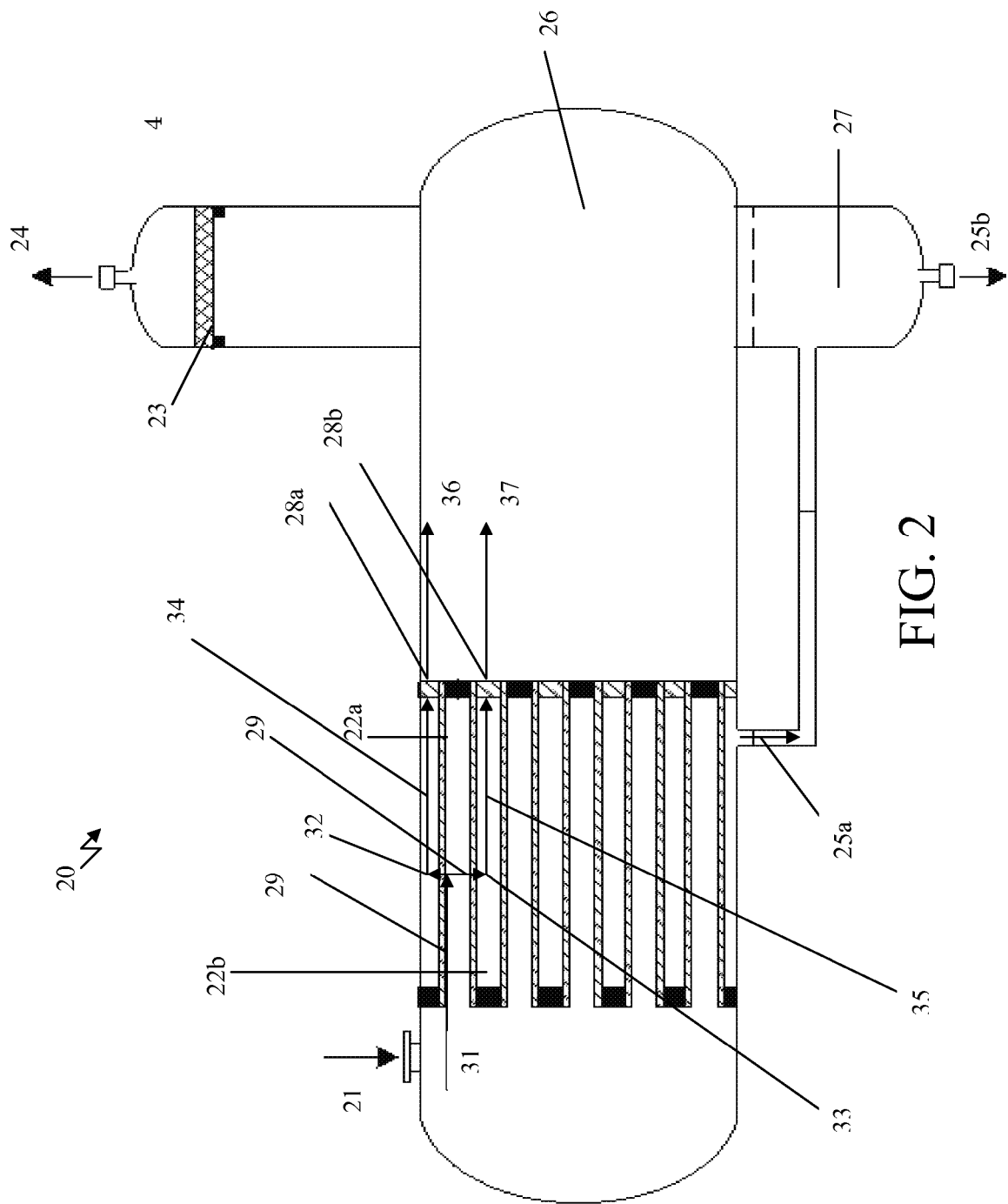
FIG. 2 is a schematic illustration of a process as disclosed herein for separating an ionic liquid from hydrocarbons by the use of a coalescer having multiple stages configured in parallel.

FIG. 2 illustrates an embodiment of the process as described herein having multiple stages oriented in parallel. As depicted in FIG. 2, a mixture 21 having ionic liquid droplets dispersed in a bulk phase of hydrocarbons is fed to a coalescer 20. The coalescer 20 contains multiple stages 22a, 22b of coalescer material oriented in parallel. In FIG. 2, the multiple stages 22a, 22b are porous pipes made from coalescer material 29, such as ceramic membrane, polymer fibers, or fiberglass, having a pore size approaching the size of the smallest droplet to be removed. The mixture enters the pipes 22a, 22b and proceeds through the pipe walls, where ionic liquid droplets are captured by coalescer material 29 to provide captured droplets that coalesce into coalesced droplets. The mixture including coalesced droplets then flows outside the pipes 22a, 22b towards vertically placed coalescer material 28a, 28b. For example, the mixture enters pipe 22a in stream 31 and proceeds through the coalescer material 29 in streams 32, 33. After ionic liquid droplets from the mixture are captured and coalesced in the walls of pipe 22a made of the coalescer material 29, the ionic liquid/hydrocarbon mixture and coalesced droplets flows outside pipe 22a in streams 34, 35. Stream 34 flows toward vertically placed coalescer material 28a and stream 35 flows toward vertically placed coalescer material 28b. Additional ionic liquid droplets entrained in the hydrocarbon phase are captured and coalesced in the vertically placed coalescer material 28a, 28b. Coalesced droplets emerge from the vertically placed coalescer material 28a, 28b in streams 36, 37 of hydrocarbons and ionic liquid. Streams 36, 37 enter a settling zone 26 wherein coalesced droplets drop through the hydrocarbons due to gravitational forces and settle into an ionic liquid layer 27 at the bottom of the settling zone. Larger droplets of coalesced ionic liquid from the porous pipes fall out of the ionic liquid/hydrocarbon mixture in stream 25a. Ionic liquid from stream 25a combines with the ionic liquid layer 7, which exits the coalescer 20 to provide an ionic liquid stream 25b. Hydrocarbons exit the settling zone 26 to provide a hydrocarbon effluent 24.

As shown in FIG. 2, the coalescer 20 can further include an additional stage 23 of coalescer material in the settling zone 26. This stage 23 is useful to prevent any ionic liquid droplets that have not been captured and coalesced in the porous pipes of coalescer material 29 and the vertically placed coalescer material 28a, 28b from exiting the coalescer 20 in the hydrocarbon effluent 24. It acts to capture and coalesce ionic liquid droplets in the same manner as the coalescer material 29 in the porous pipes and the vertically placed coalescer material 28a, 28b.

Settling Zone

A settling zone or settling zone(s) can be present in a coalescer having a single stage or a coalescer having multiple stages. A settling zone is a region in the coalescer having low turbulence. For example, it can be a pipe with low turbulence. Turbulence is undesirable in the settling zone because it can break up the coalesced droplets and re-disperse fine ionic liquid droplets into the hydrocarbons thereby frustrating the purpose of the present process. The settling zone provides an area where coalesced droplets may settle out of the bulk phase of hydrocarbons by gravity so that they can exit the reactor. Generally, coalesced droplets form an ionic liquid layer at a bottom portion of the settling zone.

Pre-Filtration

The process as described herein can further include a pre-filtration step. Such pre-filtration step involves filtering the mixture comprising hydrocarbons and ionic liquid prior to feeding the mixture to the coalescer. Such pre-filtration step removes solid particulates from the mixture and prevents the downstream coalescer from plugging or fouling. Any type of apparatus known in the art useful for removing solid particulates and having a proper pore size can be used in the pre-filtration step. For example, a self-cleaning filter, a cartridge filter, or a guard bed can be used in the pre-filtration step.

The following examples are provided to further illustrate the present process and the advantages thereof. The examples are meant to be only illustrative, and not limiting.

EXAMPLES

Example 1

Emulsification of the Hydrocarbon and Ionic Liquid Phases

Figure 3:
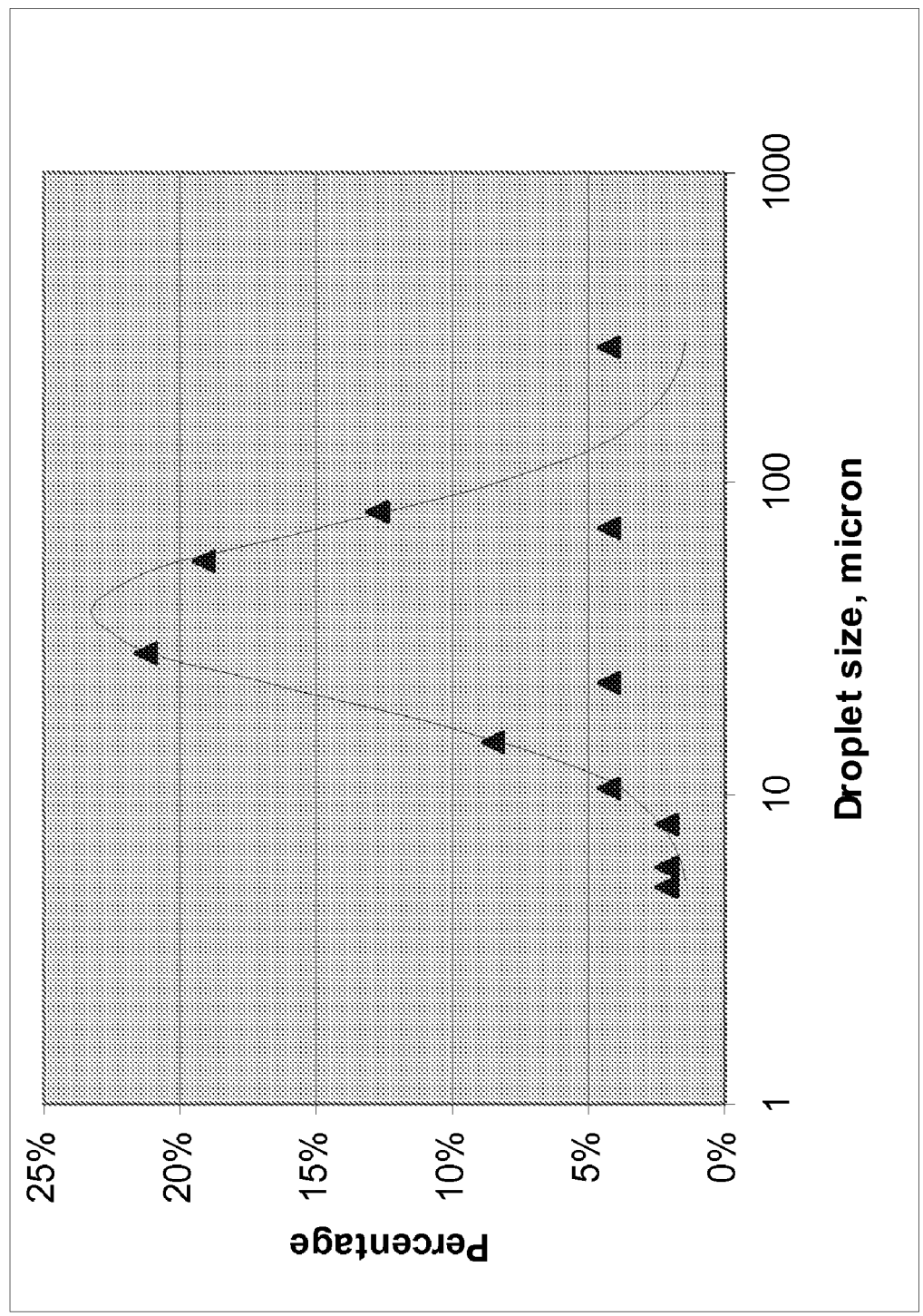
FIG. 3 is a graph depicting droplet size distribution of the hydrocarbon-ionic liquid emulsion produced in Example 1.

To provide intimate contact between the feed hydrocarbon and the ionic liquid catalyst phase for an effective alkylation reaction, a cold flow unit equipped with a nozzle was used. The experiments were conducted at ambient conditions using approximately 90 vol % of 2,2,4-trimethyl pentane (TMP) as the hydrocarbon and approximately 10 vol % ionic liquid as the catalyst phase. Two diaphragm pumps were used to feed the hydrocarbon and the catalyst phase into a tubular reactor through the nozzle. This nozzle, mounted on the top of the tubular reactor filled with TMP, had an internal mixing chamber. The hydrocarbon and catalyst feeds, fed from two separate inlets, mixed intimately in the internal chamber and exited the outlet producing a fine and near stable emulsion. If left alone, the emulsion separated naturally by gravity, usually taking 8-12 hours to fully separate indicating very fine droplets were produced. A rough droplet size distribution measurement is shown in FIG. 3 confirming the production of droplets of a few micrometers in size.

Example 2

Hydro-Cyclone for Hydrocarbon-Ionic Liquid Emulsion Separation

To separate the hydrocarbon-ionic liquid emulsion produced by a spray nozzle as discussed in Example 1, a glass hydro-cyclone was used. A large amount of ionic liquid droplets settled down in this separator, however, the hydrocarbon also contained a considerable amount of entrained droplets. Thus, there was very inefficient separation of the emulsion. A very hazy hydrocarbon effluent was obtained after the system reached steady state.

Example 3

Three Stage Coalescer for Hydrocarbon-Ionic Liquid Emulsion Separation

Figure 4:
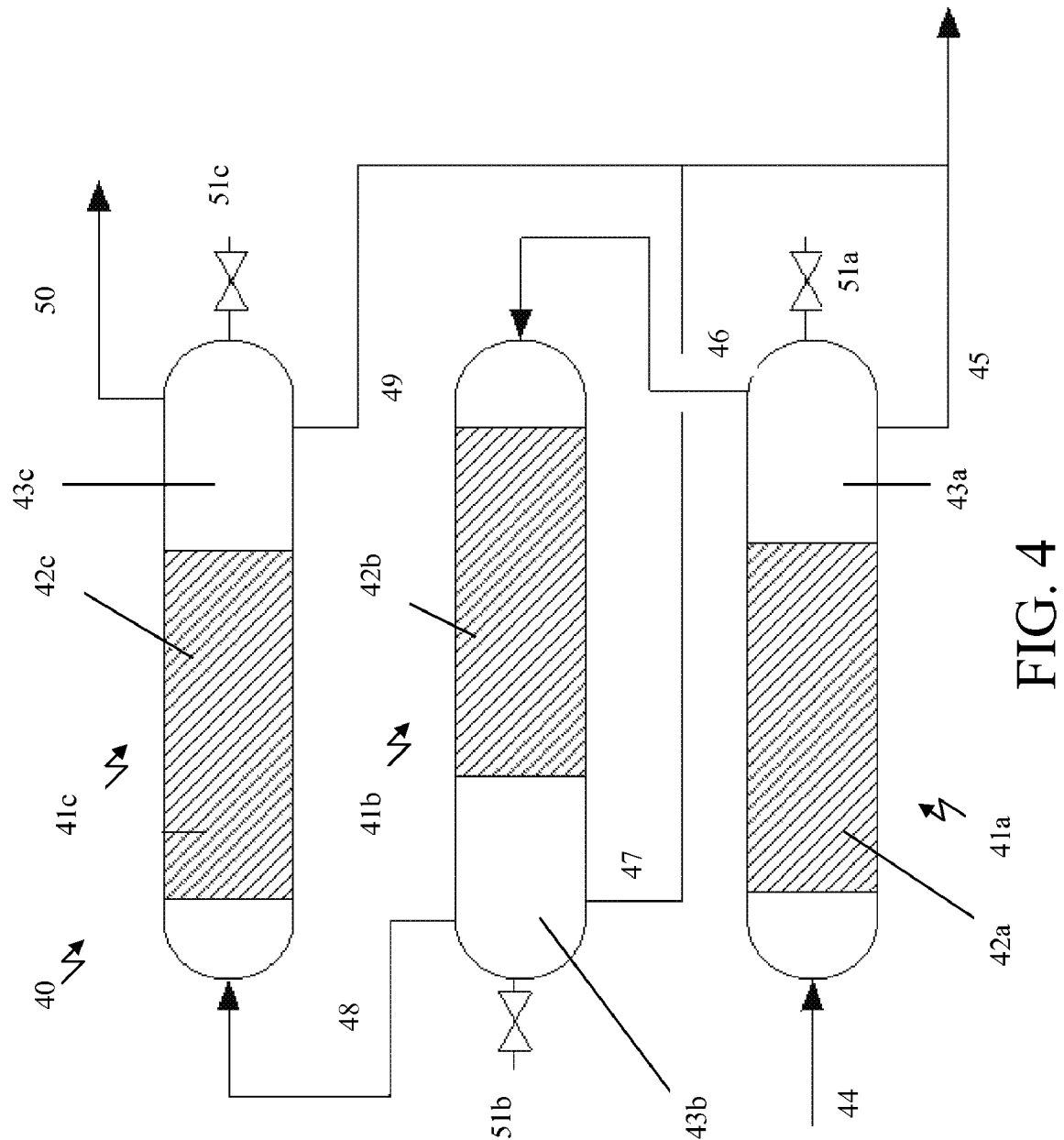
FIG. 4 is a schematic illustration of an apparatus utilized in Example 3 to separate a hydrocarbon-ionic liquid emulsion produced in Example 1.

To separate the hydrocarbon-ionic liquid emulsion produced by a spray nozzle as discussed in Example 1, a three stage coalescer apparatus where each stage was packed with different coalescer materials, as shown in FIG. 4, was used.

Each stage of this coalescer 40 was a glass pipe having a diameter of 3 inches and a length of 33 inches, providing a residence time of about 5 minutes. Each stage 41a, 41b, 41c included a coalescer material 42a, 42b, 42c having a diameter of 3 inches and a length of 24 inches, thus, leaving a settling zone 43a, 43b, 43c of about 9 inches in stages 41a, 41b, 41c. Such settling zones 43a, 43b, 43c were necessary to allow the coalesced ionic liquid droplets to settle downward. The coalescer material 42a, 42b, 42c were rather loosely packed without regard to the size of voids or openings within the coalescer material 42a, 42b, 42c. However, most of the voids or openings were larger than 100 microns. The coalescer material 42a in the first stage 41a was stainless steel, while the coalescer materials 42b, 42c in the second and third stages 41b, 41c were polytetrafluoroethylene (PTFE) and fiberglass, respectively. The three stages 41a, 41b, 41c were arranged in such a configuration that the hydrocarbon passed through the three stages 41a, 41b, 41c sequentially.

The hydrocarbon-ionic liquid emulsion was fed into the first stage 41a through pipe 44. Coalesced droplets settled into a layer of ionic liquid in the settling zone 43a, which was drained continuously through pipe 45 from the bottom of the settling zone 43a. Hydrocarbons including any remaining ionic liquid exited the first stage 41a and entered the second stage 41b through pipe 46. Coalesced droplets settled into a layer of ionic liquid in the settling zone 43b, which was drained continuously through pipe 47 from the bottom of the settling zone 43b. Hydrocarbons including any remaining ionic liquid exited the second stage 41b and entered the third stage 41c through pipe 48. Coalesced droplets settled into a layer of ionic liquid in the settling zone 43c, which was drained continuously through pipe 49 from the bottom of the settling zone 43c. Hydrocarbons including any remaining ionic liquid exited the third stage 41c through pipe 50.

To evaluate the performance of these coalescing materials, hydrocarbon samples were taken from the end of each stage through sampling ports 51a, 51b, 51c and the ionic liquid content of the hydrocarbon samples was determined. After the system reached a steady state, the measured ionic liquid content in each stage remained quite constant: approximately 1000 ppwm from the first stage, approximately 200 ppwm from the second stage, and approximately 90 ppwm from the third stage. The hydrocarbon phase effluent from the third stage 41c was observed as hazy, indicating many fine ionic liquid droplets remained in the hydrocarbon phase. This example shows the coalescer material 42a, 42b, 42c did not separate ionic liquid effectively because the coalscer material 42a, 42b, 42c was not packed to diminish voids and openings smaller than the size of the smallest droplets to be removed.

Example 4

Fiberglass Based Coalescer for Hydrocarbon-Ionic Liquid Emulsion Separation

To separate the hydrocarbon-ionic liquid emulsion produced by a spray nozzle as discussed in Example 1, a coalescer having tightly packed fiberglass was used. In this coalescer, the pores in the fiberglass were less than 10 microns. Thus, this coalescer material had a very large specific surface area and a high probability of intercepting and coalescing fine droplets. To protect this coalescer material from plugging and fouling by solid particles present in the feed stream, a prefilter with a pore size of less than 10 microns was installed upstream of the coalescer. Using the hydrocarbon-ionic liquid emulsion of Example 1 as a feed, the hydrocarbon collected at the outlet of the coalescer was crystal clear. The ionic liquid content of the hydrocarbon collected at the outlet of the coalescer was measured as about 30 ppwm.

Although the present processes have been described in connection with specific embodiments thereof, it will be appreciated by those skilled in the art that additions, deletions, modifications, and substitutions not specifically described may be made without departing from the spirit and scope of the processes as defined in the appended claims.

That which is claimed is:

1. A process for separating an ionic liquid from hydrocarbons, the process comprising:
   (a) feeding a mixture comprising hydrocarbons and ionic liquid to a coalescer, the hydrocarbons having ionic liquid droplets dispersed therein, and the coalescer comprising a coalescer material;
   (b) adhering at least a portion of the ionic liquid droplets to the coalescer material to provide captured droplets;
   (c) coalescing captured droplets into coalesced droplets; and
   (d) allowing the coalesced droplets to fall from the coalescer material to separate the ionic liquid from the hydrocarbons and provide a hydrocarbon effluent,
   wherein the coalescer material has a stronger affinity for the ionic liquid than the hydrocarbons.

2. The process according to claim 1, wherein the coalescer material is selected from the group consisting of glass beads, stainless steel metal packing, fiberglass, polymer fibers, ceramic membrane, and mixtures thereof.

3. The process according to claim 1, wherein the coalescer material is fiberglass.

4. The process according to claim 1, wherein the hydrocarbon effluent comprises 20 ppm or less of the ionic liquid.

5. The process according to claim 1, further wherein the fallen coalesced droplets provide an ionic liquid layer and further comprising (e) removing the ionic liquid layer from the coalescer and (f) removing the hydrocarbons from the coalescer to provide a hydrocarbon effluent.

6. A process for separating an ionic liquid from hydrocarbons, the process comprising:
   (a) feeding a mixture comprising hydrocarbons and ionic liquid to a coalescer, the hydrocarbons having ionic liquid droplets dispersed therein, and the coalescer comprising a coalescer material;
   (b) adhering at least a portion of the ionic liquid droplets to the coalescer material to provide captured droplets;
   (c) coalescing the captured droplets into coalesced droplets;
   (d) settling the coalesced droplets to provide an ionic liquid layer;
   (e) removing the ionic liquid layer from the coalescer; and
   (f) removing the hydrocarbons from the coalescer to provide a hydrocarbon effluent,
   wherein the coalescer material has a stronger attraction for the ionic liquid than the hydrocarbons.

7. The process according to claim 6, wherein the ionic liquid droplets have diameters between about 1 and about 1000 microns.

8. The process according to claim 6, wherein the ionic liquid droplets have diameters between about 4 microns and about 200 microns.

9. The process according to claim 6, wherein the ionic liquid droplets have a diameter of about 50 microns or greater.

10. The process according to claim 6, wherein the ionic liquid droplets have a diameter of about 5 microns or greater.

11. The process according to claim 6, wherein the hydrocarbon effluent comprises 40 ppm or less of the ionic liquid.

12. The process according to claim 6, wherein the hydrocarbon effluent comprises 20 ppm or less of the ionic liquid.

13. The process according to claim 6, wherein the hydrocarbon effluent comprises 10 ppm or less of the ionic liquid.

14. The process according to claim 6, wherein the coalescer material is selected from the group consisting of glass beads, stainless steel metal packing, fiberglass, polymer fibers, ceramic membrane, and mixtures thereof.

15. The process according to claim 14, wherein the coalescer material is fiberglass.

16. The process according to claim 6, wherein the ionic liquid is an ionic liquid catalyst.

17. The process according to claim 16, wherein the ionic liquid catalyst is a chloroaluminate ionic liquid catalyst.

18. The process according to claim 6, wherein the ionic liquid droplets comprise between 0% and about 10% by volume of the mixture comprising hydrocarbons and ionic liquid.

19. The process according to claim 6, wherein the mixture comprising hydrocarbons and ionic liquid has a residence time in the coalescer of less than about 2 hours.

20. The process according to claim 6, wherein the mixture comprising hydrocarbons and ionic liquid has a residence time in the coalescer of between about 1 minute and about 20 minutes.

21. The process according to claim 6, wherein the coalescer comprises multiple stages of coalescer material.

22. The process according to claim 6, wherein the hydrocarbons are selected from the group consisting of a product, a reactant, and mixtures thereof.

23. A process for regenerating an ionic liquid catalyst, comprising:
   (a) feeding a mixture comprising a spent ionic liquid catalyst and hydrocarbons to a coalescer, the hydrocarbons having spent ionic liquid catalyst droplets dispersed therein, and the coalescer comprising a coalescer material;
   (b) adhering at least a portion of the spent ionic liquid catalyst droplets to the coalescer material to provide captured droplets;
   (c) coalescing the captured droplets into coalesced droplets;
   (d) settling the coalesced droplets to provide a spent ionic liquid catalyst layer;
   (e) removing the spent ionic liquid catalyst layer from the coalescer to provide a spent ionic liquid catalyst stream;
   (f) removing the hydrocarbons from the coalescer to provide a hydrocarbon effluent; and
   (g) regenerating the spent ionic liquid catalyst stream to provide regenerated ionic liquid catalyst;
   wherein the coalescer material has a stronger attraction for the spent ionic liquid catalyst than the hydrocarbons.

24. An alkylation process, comprising:
   (a) conducting an alkylation reaction in the presence of an ionic liquid catalyst to provide an alkylation product and a spent ionic liquid catalyst;
   (b) feeding a mixture comprising the spent ionic liquid catalyst and the alkylation product to a coalescer, the alkylation product having spent ionic liquid catalyst droplets dispersed therein, and the coalescer comprising a coalescer material;

(c) coalescing the captured droplets into coalesced droplets;

(d) settling the coalesced droplets to provide a spent ionic liquid catalyst layer;

(e) removing the spent ionic liquid catalyst layer from the coalescer to provide a spent ionic liquid catalyst stream;

(f) removing the alkylation product from the coalescer to provide an alkylation effluent;

(g) regenerating the spent ionic liquid catalyst stream to provide regenerated ionic liquid catalyst; and (h) recycling the regenerated ionic liquid catalyst to the alkylation reaction step (a), wherein the coalescer material has a stronger attraction for the spent ionic liquid catalyst than the alkylation product.

* * * * *